United States Patent
Bernards (12)

(10) Patent No.: US 6,368,809 B1
(45) Date of Patent: Apr. 9, 2002

(54) E2F UBIQUITINATION DOMAIN, AND ASSAYS FOR INHIBITORS AND ENHANCERS OF E2F UBIQUITINATION

(75) Inventor: René Bernards, Amsterdam (NL)

(73) Assignee: Prolifix Limited, Abingdon (GB)

( * ) Notice: Subject to any disclaimer, the term of this patent is extended or adjusted under 35 U.S.C. 154(b) by 0 days.

(21) Appl. No.: 09/242,737

(22) PCT Filed: Aug. 22, 1997

(86) PCT No.: PCT/GB97/02293

§ 371 Date: Feb. 23, 1999

§ 102(e) Date: Feb. 23, 1999

(87) PCT Pub. No.: WO98/07852

PCT Pub. Date: Feb. 26, 1998

(30) Foreign Application Priority Data

Aug. 23, 1996 (GB) ............................................. 9617697

(51) Int. Cl.⁷ ................................................. G01N 33/53
(52) U.S. Cl. ............................ 435/7.1; 435/4; 435/183; 435/320.1; 536/23.5
(58) Field of Search ............................... 435/47.1, 183, 435/320.1; 536/23.5

(56) References Cited

FOREIGN PATENT DOCUMENTS

| WO | WO-9615243 A | * | 4/1996 |
| WO | 96 15243 a | | 5/1996 |

OTHER PUBLICATIONS

Black et al., Gene 237:281–301, 1999.*
Melillo et al., Mol. Cell. Biol. 14(12):8241–8249, 1994.*
Trouche et al., Proc. Natl. Acad. Sci. 93:1439–1442, Feb. 1996.*
Sardet et al., Proc. Natl. Acad. Sci. 92:2403–2407, Mar. 1995.*
Campanero et al. Proc. Natl. Acad. Sci. 94:2221–2226, Mar. 1997.*
Hateboer et al., Genes and Dev. 10(23):2960–2970, Dec. 1996.*
Hofmann et al., Genes and Dev. 10(23):2949–2959, Dec. 1996.*
Patton et al., Trends in Genetics, 14(6):236–243, Jun. 1998.
Orford et al., J. Biol. Chem., 272(40):24735–24738, Oct. 1997.
Trouche D et al: "E2F1 and E1A(12S) have a homologous activation domain regulated by RB and CBP." Proc Natl Acad Sci U S A, Feb. 20, 1996, 93 (4) P1439–42, United States, XP002047958 see p. 1439, right–hand column, paragraph 3; figure 1–3.
Sardet, Claude et al: "E2F —4 and E2F —5, two members of the E2F family, are expressed in the early phases of the cell cycle" Proc. Natl, Acad. Sci U.S.A. (1995), 92(6), 2403–7 CODEN: PNASA6:ISSN: 0027–8424, XP002048110 see abstract; figure 1 see p. 2404, right–hand column, paragraph 6– left–hand column, paragraph 1.
Campanero MR et al: "Regulation of E2F through ubiquitin–proteasom–dependent degradation: stabilization by the pRB tumor suppressor protein." Proc Natl Acad Sci U S A, Mar. 18, 1997, 94 (6) P2221–6, United States, XP002047960 see the whole document.
Hateboer G et al: "Degradation of E2F by the ubiquitin–proteasome pathway: regulation by retinoblastoma family proteins and adenovirus transforming proteins." Genes Dev., Dec. 1, 1996, 10(23) P2960–70, United States, XP002047961 see whole document.
Hofmann F et al: "The retinoblastoma gene product protects E2F–1 from degradation by the ubiquitin–proteasome pathway." Genes Dev, Dec. 1, 1996, 10 (23) P2949–59), United States, XP002047962 see whole document.

* cited by examiner

Primary Examiner—Patrick J. Nolan
(74) Attorney, Agent, or Firm—Nixon & Vanderhye P.C.

(57) ABSTRACT

The transcription factor E2F contains a ubiquitination domain. Assays for inhibitors and enhancers of the domain are provided. An assay method for an inhibitor of transcription factor E2F ubiquitin-mediated degradation comprises a) bringing a polypeptide which contains a domain which renders E2F a substrate for ubiquitination into contact with a candidate inhibitor; and b) determining whether or not the candidate inibitor is capable of reducing ubiquitination of the polypeptide. An assay method for an enhancer of transcription factor E2F ubiquitin-mediated degradation may comprise a) bringing a polypeptide which contains a domain which renders E2F a substrate for ubiquitination into contact with a candidate enhancer; and b) determining whether or not the candidate enhancer is capable of enhancing ubiquitination of said polypeptide.

15 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 1314 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1314

(xi) SEQUENCE DESCRIPTION: SEQ ID NO: 1:

```
ATG GCC TTG GCC GGG GCC CCT GCG GGC GGC CCA TGC GCG CCG GCG CTG          48
Met Ala Leu Ala Gly Ala Pro Ala Gly Gly Pro Cys Ala Pro Ala Leu
 1               5                  10                  15

GAG GCC CTG CTC GGG GCC GGC GCG CTG CGG CTG CTC GAC TCC TCG CAG          96
Glu Ala Leu Leu Gly Ala Gly Ala Leu Arg Leu Leu Asp Ser Ser Gln
                20                  25                  30

ATC GTC ATC ATC TCC GCC GCG CAG GAC GCC AGC GCC CCG CCG GCT CCC         144
Ile Val Ile Ile Ser Ala Ala Gln Asp Ala Ser Ala Pro Pro Ala Pro
            35                  40                  45

ACC GGC CCC GCG GCG CCC GCC GCC GGC CCC TGC GAC CCT GAC CTG CTG         192
Thr Gly Pro Ala Ala Pro Ala Ala Gly Pro Cys Asp Pro Asp Leu Leu
        50                  55                  60

CTC TTC GCC ACA CCG CAG GCG CCC CGG CCC ACA CCC AGT GCG CCG CGG         240
Leu Phe Ala Thr Pro Gln Ala Pro Arg Pro Thr Pro Ser Ala Pro Arg
 65                  70                  75                  80

CCC GCG CTC GGC CGC CCG CCG GTG AAG CGG AGG CTG GAC CTG GAA ACT         288
Pro Ala Leu Gly Arg Pro Pro Val Lys Arg Arg Leu Asp Leu Glu Thr
                85                  90                  95

GAC CAT CAG TAC CTG GCC GAG AGC AGT GGG CCA GCT CGG GGC AGA GGC         336
Asp His Gln Tyr Leu Ala Glu Ser Ser Gly Pro Ala Arg Gly Arg Gly
                100                 105                 110

CGC CAT CCA GGA AAA GGT GTG AAA TCC CCG GGG GAG AAG TCA CGC TAT         384
Arg His Pro Gly Lys Gly Val Lys Ser Pro Gly Glu Lys Ser Arg Tyr
            115                 120                 125

GAG ACC TCA CTG AAT CTG ACC ACC AAG CGC TTC CTG GAG CTG CTG AGC         432
Glu Thr Ser Leu Asn Leu Thr Thr Lys Arg Phe Leu Glu Leu Leu Ser
        130                 135                 140

CAC TCG GCT GAC GGT GTC GTC GAC CTG AAC TGG GCT GCC GAG GTG CTG         480
His Ser Ala Asp Gly Val Val Asp Leu Asn Trp Ala Ala Glu Val Leu
145                 150                 155                 160
```

-continued

```
AAG GTG CAG AAG CGG CGC ATC TAT GAC ATC ACC AAC GTC CTT GAG GGC         528
Lys Val Gln Lys Arg Arg Ile Tyr Asp Ile Thr Asn Val Leu Glu Gly
            165                 170                 175

ATC CAG CTC ATT GCC AAG AAG TCC AAG AAC CAC ATC CAG TGG CTG GGC         576
Ile Gln Leu Ile Ala Lys Lys Ser Lys Asn His Ile Gln Trp Leu Gly
        180                 185                 190

AGC CAC ACC ACA GTG GGC GTC GGC GGA CGG CTT GAG GGG TTG ACC CAG         624
Ser His Thr Thr Val Gly Val Gly Gly Arg Leu Glu Gly Leu Thr Gln
        195                 200                 205

GAC CTC CGA CAG CTG CAG GAG AGC GAG CAG CAG CTG GAC CAC CTG ATG         672
Asp Leu Arg Gln Leu Gln Glu Ser Glu Gln Gln Leu Asp His Leu Met
    210                 215                 220

AAT ATC TGT ACT ACG CAG CTG CGC CTG CTC TCC GAG GAC ACT GAC AGC         720
Asn Ile Cys Thr Thr Gln Leu Arg Leu Leu Ser Glu Asp Thr Asp Ser
225                 230                 235                 240

CAG CGC CTG GCC TAC GTG ACG TGT CAG GAC CTT CGT AGC ATT GCA GAC         768
Gln Arg Leu Ala Tyr Val Thr Cys Gln Asp Leu Arg Ser Ile Ala Asp
            245                 250                 255

CCT GCA GAG CAG ATG GTT ATG GTG ATC AAA GCC CCT CCT GAG ACC CAG         816
Pro Ala Glu Gln Met Val Met Val Ile Lys Ala Pro Pro Glu Thr Gln
        260                 265                 270

CTC CAA GCC GTG GAC TCT TCG GAG AAC TTT CAG ATC TCC CTT AAG AGC         864
Leu Gln Ala Val Asp Ser Ser Glu Asn Phe Gln Ile Ser Leu Lys Ser
        275                 280                 285

AAA CAA GGC CCG ATC GAT GTT TTC CTG TGC CCT GAG GAG ACC GTA GGT         912
Lys Gln Gly Pro Ile Asp Val Phe Leu Cys Pro Glu Glu Thr Val Gly
    290                 295                 300

GGG ATC AGC CCT GGG AAG ACC CCA TCC CAG GAG GTC ACT TCT GAG GAG         960
Gly Ile Ser Pro Gly Lys Thr Pro Ser Gln Glu Val Thr Ser Glu Glu
305                 310                 315                 320

GAG AAC AGG GCC ACT GAC TCT GCC ACC ATA GTG TCA CCA CCA CCA TCA        1008
Glu Asn Arg Ala Thr Asp Ser Ala Thr Ile Val Ser Pro Pro Pro Ser
            325                 330                 335

TCT CCC CCC TCA TCC CTC ACC ACA GAT CCC AGC CAG TCT CTA CTC AGC        1056
Ser Pro Pro Ser Ser Leu Thr Thr Asp Pro Ser Gln Ser Leu Leu Ser
        340                 345                 350

CTG GAG CAA GAA CCG CTG TTG TCC CGG ATG GGC AGC CTG CGG GCT CCC        1104
Leu Glu Gln Glu Pro Leu Leu Ser Arg Met Gly Ser Leu Arg Ala Pro
        355                 360                 365

GTG GAC GAG GAC CGC CTG TCC CCG CTG GTG GCG GCC GAC TCG CTC CTG        1152
Val Asp Glu Asp Arg Leu Ser Pro Leu Val Ala Ala Asp Ser Leu Leu
370                 375                 380

GAG CAT GTG CGG GAG GAC TTC TCC GGC CTC CTC CCT GAG GAG TTC ATC        1200
Glu His Val Arg Glu Asp Phe Ser Gly Leu Leu Pro Glu Glu Phe Ile
385                 390                 395                 400

AGC CTT TCC CCA CCC CAC GAG GCC CTC GAC TAC CAC TTC GGC CTC GAG        1248
Ser Leu Ser Pro Pro His Glu Ala Leu Asp Tyr His Phe Gly Leu Glu
            405                 410                 415

GAG GGC GAG GGC ATC AGA GAC CTC TTC GAC TGT GAC TTT GGG GAC CTC        1296
Glu Gly Glu Gly Ile Arg Asp Leu Phe Asp Cys Asp Phe Gly Asp Leu
        420                 425                 430

ACC CCC CTG GAT TTC TGA                                                1314
Thr Pro Leu Asp Phe
        435
```

(2) INFORMATION FOR SEQ ID NO: 2:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Leu Ala Gly Ala Pro Ala Gly Gly Pro Cys Ala Pro Ala Leu
 1               5                  10                  15

Glu Ala Leu Leu Gly Ala Gly Ala Leu Arg Leu Leu Asp Ser Ser Gln
                 20                  25                  30

Ile Val Ile Ile Ser Ala Ala Gln Asp Ala Ser Ala Pro Pro Ala Pro
             35                  40                  45

Thr Gly Pro Ala Ala Pro Ala Ala Gly Pro Cys Asp Pro Asp Leu Leu
     50                  55                  60

Leu Phe Ala Thr Pro Gln Ala Pro Arg Pro Thr Pro Ser Ala Pro Arg
 65                  70                  75                  80

Pro Ala Leu Gly Arg Pro Pro Val Lys Arg Arg Leu Asp Leu Glu Thr
                 85                  90                  95

Asp His Gln Tyr Leu Ala Glu Ser Ser Gly Pro Ala Arg Gly Arg Gly
                100                 105                 110

Arg His Pro Gly Lys Gly Val Lys Ser Pro Gly Glu Lys Ser Arg Tyr
            115                 120                 125

Glu Thr Ser Leu Asn Leu Thr Thr Lys Arg Phe Leu Glu Leu Leu Ser
130                 135                 140

His Ser Ala Asp Gly Val Val Asp Leu Asn Trp Ala Ala Glu Val Leu
145                 150                 155                 160

Lys Val Gln Lys Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
                180                 185                 190

Ser His Thr Thr Val Gly Val Gly Gly Arg Leu Glu Gly Leu Thr Gln
            195                 200                 205

Asp Leu Arg Gln Leu Gln Glu Ser Glu Gln Gln Leu Asp His Leu Met
    210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
                260                 265                 270

Leu Gln Ala Val Asp Ser Ser Glu Asn Phe Gln Ile Ser Leu Lys Ser
            275                 280                 285

Lys Gln Gly Pro Ile Asp Val Phe Leu Cys Pro Glu Glu Thr Val Gly
290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Ser
                325                 330                 335

Ser Pro Pro Ser Ser Leu Thr Thr Asp Pro Ser Gln Ser Leu Leu Ser
            340                 345                 350

Leu Glu Gln Glu Pro Leu Leu Ser Arg Met Gly Ser Leu Arg Ala Pro
            355                 360                 365

Val Asp Glu Asp Arg Leu Ser Pro Leu Val Ala Ala Asp Ser Leu Leu
    370                 375                 380

Glu His Val Arg Glu Asp Phe Ser Gly Leu Leu Pro Glu Glu Phe Ile
385                 390                 395                 400
```

```
Ser Leu Ser Pro Pro His Glu Ala Leu Asp Tyr His Phe Gly Leu Glu
            405                 410                 415

Glu Gly Glu Gly Ile Arg Asp Leu Phe Asp Cys Asp Phe Gly Asp Leu
            420                 425                 430

Thr Pro Leu Asp Phe
            435

(2) INFORMATION FOR SEQ ID NO: 3:

(i) SEQUENCE CHARACTERISTICS:
        (A) LENGTH: 1489 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 27..1268

(xi) SEQUENCE DESCRIPTION: SEQ ID NO: 3:

CAGTCGACCC CGGGGCGGCG GGCGCG ATG GCG GAG GCC GGG CCA CAG GCG CCG        53
                            Met Ala Glu Ala Gly Pro Gln Ala Pro
                              1               5

CCG CCC CCG GGG ACT CCA AGC CGG CAC GAA AAG AGC CTG GGA CTG CTC       101
Pro Pro Pro Gly Thr Pro Ser Arg His Glu Lys Ser Leu Gly Leu Leu
 10              15                  20                  25

ACC ACC AAG TTC GTG TCC CTT CTG CAG GAG GCC AAG GAC GGC GTG CTT       149
Thr Thr Lys Phe Val Ser Leu Leu Gln Glu Ala Lys Asp Gly Val Leu
                 30                  35                  40

GAC CTC AAG CTG GCA GCT GAC ACC CTA GCT GTA CGC CAG AAG CGG CGG       197
Asp Leu Lys Leu Ala Ala Asp Thr Leu Ala Val Arg Gln Lys Arg Arg
             45                  50                  55

ATT TAC GAC ATT ACC AAT GTT TTG GAA GGT ATC GGG CTA ATC GAG AAA       245
Ile Tyr Asp Ile Thr Asn Val Leu Glu Gly Ile Gly Leu Ile Glu Lys
         60                  65                  70

AAG TCC AAG AAC AGC ATC CAG TGG AAG GGT GTG GGG CCT GGC TGC AAT       293
Lys Ser Lys Asn Ser Ile Gln Trp Lys Gly Val Gly Pro Gly Cys Asn
     75                  80                  85

ACC CGG GAG ATT GCT GAC AAA CTG ATT GAG CTC AAG GCA GAG ATC GAG       341
Thr Arg Glu Ile Ala Asp Lys Leu Ile Glu Leu Lys Ala Glu Ile Glu
 90                  95                 100                 105

GAG CTG CAG CAG CGG GAG CAA GAA CTA GAC CAG CAC AAG GTG TGG GTG       389
Glu Leu Gln Gln Arg Glu Gln Glu Leu Asp Gln His Lys Val Trp Val
                110                 115                 120

CAG CAG AGC ATC CGG AAC GTC ACA GAG GAC GTG CAG AAC AGC TGT TTG       437
Gln Gln Ser Ile Arg Asn Val Thr Glu Asp Val Gln Asn Ser Cys Leu
            125                 130                 135

GCC TAC GTC ACT CAT GAG GAC ATC TGC AGA TGC TTT GCT GGA GAT ACC       485
Ala Tyr Val Thr His Glu Asp Ile Cys Arg Cys Phe Ala Gly Asp Thr
        140                 145                 150

CTC TTG GCC ATC CGG GCC CCA TCA GGC ACC AGC CTG GAG GTG CCC ATC       533
Leu Leu Ala Ile Arg Ala Pro Ser Gly Thr Ser Leu Glu Val Pro Ile
    155                 160                 165

CCA GAG GGT CTC AAT GGG CAG AAG AAG TAC CAG ATT CAC CTG AAG AGT       581
Pro Glu Gly Leu Asn Gly Gln Lys Lys Tyr Gln Ile His Leu Lys Ser
170                 175                 180                 185

GTG AGT GGT CCC ATT GAG GTT CTG CTG GTG AAC AAG GAG GCA TGG AGC       629
Val Ser Gly Pro Ile Glu Val Leu Leu Val Asn Lys Glu Ala Trp Ser
                190                 195                 200

TCA CCC CCT GTG GCT GTG CCT GTG CCA CCA CCT GAA GAT TTG CTC CAG       677
Ser Pro Pro Val Ala Val Pro Val Pro Pro Pro Glu Asp Leu Leu Gln
            205                 210                 215
```

```
AGC CCA TCT GCT GTT TCT ACA CCT CCA CCT CTG CCC AAG CCT GCC CTA     725
Ser Pro Ser Ala Val Ser Thr Pro Pro Pro Leu Pro Lys Pro Ala Leu
        220                 225                 230

GCC CAG TCC CAG GAA GCC TCA CGT CCA AAT AGT CCT CAG CTC ACT CCC     773
Ala Gln Ser Gln Glu Ala Ser Arg Pro Asn Ser Pro Gln Leu Thr Pro
    235                 240                 245

ACT GCT GTC CCT GGC AGT GCA GAA GTC CAG GGA ATG GCT GGC CCA GCA     821
Thr Ala Val Pro Gly Ser Ala Glu Val Gln Gly Met Ala Gly Pro Ala
250                 255                 260                 265

GCT GAG ATC ACA GTG AGT GGC GGC CCT GGG ACT GAT AGC AAG GAC AGT     869
Ala Glu Ile Thr Val Ser Gly Gly Pro Gly Thr Asp Ser Lys Asp Ser
            270                 275                 280

GGT GAG CTC AGT TCA CTC CCA CTG GGC CCA ACA ACA CTG GAC ACC CGG     917
Gly Glu Leu Ser Ser Leu Pro Leu Gly Pro Thr Thr Leu Asp Thr Arg
        285                 290                 295

CCA CTG CAG TCT TCT GCC CTG CTG GAC AGC AGC AGC AGC AGC AGC AGC     965
Pro Leu Gln Ser Ser Ala Leu Leu Asp Ser Ser Ser Ser Ser Ser Ser
    300                 305                 310

AGC AGC AGC AGC AGC AGC AAC AGT AAC AGC AGC AGT TCG TCC GGA CCC    1013
Ser Ser Ser Ser Ser Ser Asn Ser Asn Ser Ser Ser Ser Gly Pro
315                 320                 325

AAC CCT TCT ACC TCC TTT GAG CCC ATC AAG GCA GAC CCC ACA GGT GTT    1061
Asn Pro Ser Thr Ser Phe Glu Pro Ile Lys Ala Asp Pro Thr Gly Val
330                 335                 340                 345

TTG GAA CTC CCC AAA GAG CTG TCA GAA ATC TTT GAT CCC ACA CGA GAG    1109
Leu Glu Leu Pro Lys Glu Leu Ser Glu Ile Phe Asp Pro Thr Arg Glu
            350                 355                 360

TGC ATG AGC TCG GAG CTG CTG GAG GAG TTG ATG TCC TCA GAA GTG TTT    1157
Cys Met Ser Ser Glu Leu Leu Glu Glu Leu Met Ser Ser Glu Val Phe
        365                 370                 375

GCC CCT CTG CTT CGT CTT TCT CCA CCC CCG GGA GAC CAC GAT TAT ATC    1205
Ala Pro Leu Leu Arg Leu Ser Pro Pro Pro Gly Asp His Asp Tyr Ile
    380                 385                 390

TAC AAC CTG GAC GAG AGT GAA GGT GTC TGT GAC CTC TTT GAT GTG CCT    1253
Tyr Asn Leu Asp Glu Ser Glu Gly Val Cys Asp Leu Phe Asp Val Pro
395                 400                 405

GTT CTC AAC CTC TGACTGACAG GGACATGCCC TGTGTGGCTG GGACCCAGAC        1305
Val Leu Asn Leu
410

TGTCTGACCT GGGGGTTGCC TGGGGACCTC TCCCACCCGA CCCCTACAGA GCTTGAGA    1365

CACAGACGCC TGGCTTCTCC GGNATTNCCT TACCGCACAG TTCTGGCCAC ACGTCCCG    1425

CCTGTGCTGG CACTTCTGTG CTCGCAGAGC AGGGGAACAG GACTCAGCCC CCATCACC    1485

GGAG                                                              1489

(2) INFORMATION FOR SEQ ID NO: 4:

(i) SEQUENCE CHARACTERISTICS:
        (A) LENGTH: 413 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Glu Ala Gly Pro Gln Ala Pro Pro Pro Gly Thr Pro Ser
 1               5                  10                  15

Arg His Glu Lys Ser Leu Gly Leu Leu Thr Thr Lys Phe Val Ser Leu
            20                  25                  30
```

-continued

```
Leu Gln Glu Ala Lys Asp Gly Val Leu Asp Leu Lys Leu Ala Ala Asp
         35                  40                  45

Thr Leu Ala Val Arg Gln Lys Arg Arg Ile Tyr Asp Ile Thr Asn Val
     50                  55                  60

Leu Glu Gly Ile Gly Leu Ile Glu Lys Ser Lys Asn Ser Ile Gln
 65                  70                  75                  80

Trp Lys Gly Val Gly Pro Gly Cys Asn Thr Arg Glu Ile Ala Asp Lys
                 85                  90                  95

Leu Ile Glu Leu Lys Ala Glu Ile Glu Glu Leu Gln Gln Arg Glu Gln
                100                 105                 110

Glu Leu Asp Gln His Lys Val Trp Val Gln Gln Ser Ile Arg Asn Val
             115                 120                 125

Thr Glu Asp Val Gln Asn Ser Cys Leu Ala Tyr Val Thr His Glu Asp
         130                 135                 140

Ile Cys Arg Cys Phe Ala Gly Asp Thr Leu Leu Ala Ile Arg Ala Pro
145                 150                 155                 160

Ser Gly Thr Ser Leu Glu Val Pro Ile Pro Glu Gly Leu Asn Gly Gln
                165                 170                 175

Lys Lys Tyr Gln Ile His Leu Lys Ser Val Ser Gly Pro Ile Glu Val
             180                 185                 190

Leu Leu Val Asn Lys Glu Ala Trp Ser Ser Pro Val Ala Val Pro
         195                 200                 205

Val Pro Pro Pro Glu Asp Leu Leu Gln Ser Pro Ser Ala Val Ser Thr
210                 215                 220

Pro Pro Pro Leu Pro Lys Pro Ala Leu Ala Gln Ser Gln Glu Ala Ser
225                 230                 235                 240

Arg Pro Asn Ser Pro Gln Leu Thr Pro Thr Ala Val Pro Gly Ser Ala
                245                 250                 255

Glu Val Gln Gly Met Ala Gly Pro Ala Ala Glu Ile Thr Val Ser Gly
             260                 265                 270

Gly Pro Gly Thr Asp Ser Lys Asp Ser Gly Glu Leu Ser Ser Leu Pro
         275                 280                 285

Leu Gly Pro Thr Thr Leu Asp Thr Arg Pro Leu Gln Ser Ser Ala Leu
     290                 295                 300

Leu Asp Ser Ser Ser Ser Ser Ser Ser Ser Ser Ser Ser Ser Ser Asn
305                 310                 315                 320

Ser Asn Ser Ser Ser Ser Gly Pro Asn Pro Ser Thr Ser Phe Glu
                325                 330                 335

Pro Ile Lys Ala Asp Pro Thr Gly Val Leu Glu Leu Pro Lys Glu Leu
             340                 345                 350

Ser Glu Ile Phe Asp Pro Thr Arg Glu Cys Met Ser Ser Glu Leu Leu
         355                 360                 365

Glu Glu Leu Met Ser Ser Glu Val Phe Ala Pro Leu Leu Arg Leu Ser
     370                 375                 380

Pro Pro Pro Gly Asp His Asp Tyr Ile Tyr Asn Leu Asp Glu Ser Glu
385                 390                 395                 400

Gly Val Cys Asp Leu Phe Asp Val Pro Val Leu Asn Leu
                405                 410
```

E2F UBIQUITINATION DOMAIN, AND ASSAYS FOR INHIBITORS AND ENHANCERS OF E2F UBIQUITINATION

This application is a national stage filing under U.S.C. 371 from PCT/GB97/02293.

The present invention relates to the interaction of transcription factor E2F with ubiquitin, and to assays for modulators of this interaction.

E2F transcription factors control the expression of at least three groups of genes that are involved in cell cycle regulation. First, E2F sites have been found in the promoter of the immediate early gene c-myc (Hiebert et al., 1989; Oswald et al., 1994). In addition, E2F contributes to the regulation of several genes whose expression is activated in the G1 phase of the cell cycle, including cyclin E, E2F-1 and p107 (Degregori et al., 1995; Johnson et al., 1994; Neuman et al., 1994; Zhu et al., 1995). Finally, E2F contributes to the cell cycle-regulated expression of a number of genes that are required during S phase, such as cyclin A, dihydrofolate reductase, DNA polymerase a and thymidine kinase (reviewed by Farnham et al., 1993). E2F transcription factors are heterodimers that contain one of five related E2F polypeptides and one of two DP polypeptides (reviewed by Beijersbergen and Bernards, 1996).

The activity of the various E2F transcription factors is regulated at three different levels. First, the abundance of E2F is regulated at the level of transcription. For example, E2F-4 is the most prominent E2F species in quiescent cells, whereas E2F-1 is absent from quiescent cells and is transcriptionally induced in late G1 after serum stimulation (Johnson et al., 1994; Sardet et al., 1995). Second, transactivation by E2Fs is negatively regulated by complex formation with one of three members of the retinoblastoma pocket protein family, pRb, p107 and p130 (reviewed by Beijersbergen and Bernards, 1996). E2F-1, 2, and 3 interact preferentially with pRb; E2F-4 with p107 and p130 (Beijersbergen et al., 1994; Ginsberg et al., 1994; Vairo et al., 1995); E2F-5 with p130 only (Hijmans et al., 1995). These E2F-pocket protein complexes are likely to perform different functions during the cell cycle as the timing of their appearance differs. Most quiescent cells have one major E2F complex that consists of E2F-4 in complex with p130 (Chittenden et al., 1993; Cobrinik et al., 1993; Vairo et al., 1995). Exponentially growing cells contain significant amounts of free E2F and E2F-p107 complexes (Beijersbergen et al., 1995; Cobrinik et al., 1993; Lees et al., 1992; Shirodkar et al., 1992). E2F-pocket protein complexes are regulated by phosphorylation of the pocket proteins by G1 cyclin/cyclin-dependent kinase (cdk) complexes. pRb can be phosphorylated by cyclin D/cdk4, cyclin E/cdk2 and cyclin A/cdk2 kinase complexes (Dowdy et al., 1993; Ewen et al., 1993; Hinds et al., 1992). In contrast, p107 is only efficiently phosphorylated by cyclin D/cdk4 (Beijersbergen et al., 1995). In addition, several viral oncoproteins, including adenovirus E1A, can disrupt E2F-pocket protein complexes through high affinity binding to the pocket proteins (Whyte et al., 1988). A third level of regulation of E2F activity concerns the regulation of DNA binding activity. Krek et al. (1994) have shown that E2F-1 can interact directly with cyclin A, which results in phosphorylation of DP-1 in S phase, causing down-regulation of E2F DNA binding activity. Down-regulation of E2F in S phase appears to be important in cellular homeostasis, as over-expression of E2F, or mutants of E2F that resist cyclin A down-regulation, can cause apoptosis and transformation (Beijersbergen et al., 1994; Johnson et al., 1994; Krek et al., 1995; Qin et al., 1994; Singh et al., 1994; Wu and Levine, 1994).

E2F DNA binding sites in promoters can act both as positive and negative regulatory elements, depending on the promoter context (Lam and Watson, 1993). The action of E2F sites as negative regulatory elements is most readily explained by the finding that pocket proteins can mediate active transcriptional Thus, E2F/pocket protein complexes found in quiescent cells may contribute to maintaining quiescence through active transcriptional silencing of growth factor-activated genes.

Many of the proteins that contribute to regulation of the cell cycle appear and disappear rapidly, often in a cell cycle-regulated manner. Degradation of unstable proteins frequently involves the ubiquitin-proteasome pathway (Hilt and Wolf, 1996; Hochstrasser, 1995; Jentsch, 1992; Jentsch and Schlenker, 1995; Rubin and Finley, 1995). This system acts by covalent attachment of multiple ubiquitin polypeptides to the substrate. Ubiquitin is a highly conserved 76 amino acid protein found in eukaryotic cells. Ubiquitination requires the action of three different enzymes. A ubiquitin-activating enzyme (E1), which binds ubiquitin and transfers it to an ubiquitin conjugating enzyme (UBC or E2) (Haas and Rose, 1982; Pickart and Rose, 1985), which in turn may need the assistance of a ubiquitin ligase (E3) to attach the ubiquitin residue covalently to the substrate at a lysine residue. Each ubiquitin covalently attached to a lysine residue of the substrate protein is further ubiquitinated at a lysine residue in the ubiquitin sequence itself. Multi-ubiquitination acts as a sorting signal which targets substrates for rapid degradation by the proteasome, a complex of proteolytic enzymes (Chau et al., 1989).

An important link between the ubiquitin-proteasome machinery and cell cycle regulation came from the finding that CDC34, a yeast gene required for the G1 to S transition, was identical to yeast UBC3, a ubiquitin conjugating enzyme (Goebl et al., 1994). Other substrates of Cdc34 include yeast G1 cyclins and the cyclin/cdk inhibitor p40$^{sic1}$ (Deshaies et al., 1995; Schwob et al., 1994; Yaglom et al., 1995). In mammalian cells, the p27 cyclin/cdk inhibitor was recently shown to be a degraded in a cell cycle dependent fashion by the ubiquitin-proteasome pathway (Pagano et al., 1995). In budding yeast, the S-phase cyclin Clb5 and the mitotic cyclin Clb2 are ubiquitinated through UBC9 (Seufert et al., 1995) and Xenopus mitotic cyclins have also been shown to be degraded through ubiquitination (Glotzer et al., 1991).

We report here that E2F transcription factors are unstable due to destruction by the ubiquitin-proteasome pathway and that their degradation is highly regulated.

Accordingly, the present invention provides an assay method for an inhibitor of transcription factor E2F ubiquitin-mediated degradation which method comprises:

a) bringing a polypeptide which contains a domain which renders E2F a substrate for ubiquitination into contact with a candidate inhibitor; and b) determining whether or not the candidate inhibitor is capable of reducing ubiquintination of said polypeptide.

The polypeptide may be an E2F protein or fragment thereof which is capable of binding to a pocket protein or the polypeptide may comprise an indicator polypeptide such as LacZ.

Preferably, the domain which renders E2F a substrate for ubiquitination comprises the 63 amino acid C-terminal region of E2F-l, or the 138 amino acid C-terminal domain of E2F-4, or portion thereof such as the 112 C-terminal amino acids.

The assay will normally be conducted in a format where the polypeptide is expressed in a host cell from a recombinant expression vector, such as an expression vector where the polypeptide is operably linked to a CMV promoter.

In one embodiment, a DP-1 polypeptide is co-expressed in the host cell.

Assays of the invention may be conducted in the presence of a proteasome inhibitor.

In the assay of the invention the determining of whether or not the candidate inhibitor is capable of reducing ubiquintination of said polypeptide may be performed by providing ubiquitin and determining the amount of said ubiquitin which has been bound to said polypeptide. This may be achieved by ubiquitin or contains an expression vector capable of expressing ubiquitin. The ubiquitin may be tagged with an epitope capable of binding to a monoclonal antibody, such as an HA epitope.

In another aspect, the invention also provides a vector which comprises a nucleotide sequence encoding a truncated E2F polypeptide wherein said truncated polypeptide does not contain a C-terminal domain capable of ubiquitination. One such polypeptide is E2F-1 1–374.

In a further aspect, the invention also provides an assay method for an enhancer of transcription factor E2F ubiquitin-mediated degradation which method comprises:

a) bringing polypeptide which contains a domain which renders E2F a substrate for ubiquitination into contact with a candidate promoter; and b) determining whether or not the candidate promoter is capable of enhancing ubiquintination of said polypeptide.

The various preferred embodiments of the assay for inhibitors described herein may also be used in this further aspect of the invention.

The amino acid sequences of E2F-1 and E2F-4 are shown as SEQ. ID NO.1 and SEQ. ID No.4 respectively.

DETAILED DESCRIPTION OF THE INVENTION

In the present application, reference to transcription factor E2F refers to the family of transcription factors capable of forming a heterodimer with a DP-transcription factor as described by Beijerbergen and Bernards, 1996, (the disclosure of which is incorporated herein by reference) and capable of forming a complex with a member of the retinoblastoma pocket protein family, such as pRb, p107 or p130.

E2F proteins are found in mammalian cells. Representative of specific members of the E2F family are those members found in human cells. For example, human E2F-1 is shown as SEQ ID NO. 1. Human E2F-2 and E2F-3 are disclosed in, for example, Lees et al (1993) Mol.Cell.Biol 13; 7813–7825, the disclosure of which is incorporated herein by reference. Human E2F-4 is shown as SEQ ID NO. 3. Human E2F-5 is disclosed in, for example, WO/96/25494, the disclosure of which is incorporated herein by reference.

E2F proteins from other species, such as mice, are also available or may be cloned using standard methodology known in the art per se and by reference to the techniques used to clone the human E2F proteins mentioned above.

Synthetic variants of the human or other species E2F proteins may be used. Synthetic variants include those which have at least 80%, preferably at least 90%, homology to human E2F-1 or E2F-4. More preferably such variants correspond to the sequence of said human E2F-1 or E2F-4 but have one or more, e.g. from 1 to 20, such as from 2, 5 or 10 substitutions, deletions or insertions of amino acids.

Such variants will desirably retain one or both of the following functional properties:

(i) the ability to cause the E2F protein to undergo ubiquitin-mediated degradation as described herein for the various specific E2F proteins exemplified; and (ii) the ability to bind to a pocket protein.

Both functional properties may be determined by routine experimentation by reference to methods illustrated in the accompanying examples.

The assay method for modulators of E2F ubiquitin-mediated degradation is useful in determining candidate substances which can influence the progression of the cell cycle. This is because E2F is required in cell cycle control and its modulation may influence progression or arrest of the cycle or may induce apoptosis. Thus modulator substances which are capable of reducing or increasing ubiquitination of E2F will be useful in arresting the cell cycle. Such substances will be useful in research, for example in providing synchronous populations of example in the treatment of proliferative diseases such as cancer.

The assay may be conducted in any suitable format designed to examine the interaction of E2F with ubiquitin. For example, the assay could be conducted in an in vitro cell-free system in which the polypeptide, inhibitor substance and ubiquitin are provided together with other cellular components involved in the ubiquitination process. A rabbit reticulocyte lysate may be used as the basis for a cell free system, supplemented with a ubiquitin activating enzyme (E1) and ATP.

Preferably however the assay is conducted in a host cell which contains an expression vector capable of expressing the E2F polypeptide. The host cell may also contain a further expression vector capable of expressing a DP-polypeptide such as DP-1. The host cell may also contain a vector capable of expressing ubiquitin. Any or all of the polypeptides encoded by the expression vectors may include an epitope which is capable of being detected by a monoclonal antibody. The epitope is generally one which is not normally present in the host cell such as the HA epitope of influenza virus.

Where a vector encoding a ubiquitin is supplied to the assay of the invention, the ubiquitin encoded by the vector may be any suitable ubiquitin compatible with the host cell or in vitro assay system being used. For example, various mammalian ubiquitins have been characterised and their sequences may be obtained by reference to the published literature or databases. As indicated above, the ubiquitin may be tagged with an epitope detectable by an antibody and this epitope may be fused to the N- or C- terminal of the ubiquitin.

Generally, naturally occuring sequences of ubiquitin will be used, for example mammalian, preferably human, although minor modifications to the sequences may be made, for example during the engineering of nucleic acid encoding ubiquitin into a sequence encoding an epitope some residues may be altered or deleted. An example of a vector encoding ubiquitin may be found in Treier et al, 1994, the disclosure of which is incorporated herein by reference.

The host cell may be any suitable host cell in which ubiquitination of E2F can occur. The suitability of host cells may be determined by repeating procedures analogous to those described in accompanying Examples in a potential host cell and determining whether ubiquitination of E2F occurs. Suitable host cells include mammalian host cells such as human or murine host cells. Other host cells include insect or yeast host cells.

Although a naturally-occurring E2F protein or synthetic variant thereof may be used the assay may be conducted with other polypeptides such as fusion proteins which retain the domain of E2F which renders E2F a substrate for ubiquitination. We have found this domain is present in the C-terminal region of E2F. The experiments described in the accompanying Examples demonstrate that this region is contained within the 63 C-terminal amino acids of E2F-1 although smaller portions of this region may also be used provided they retain their substrate function. Thus for example a fragment of this 63 amino acid region comprising 10, 20, 30, 40 or 50 amino acids may be used provided such a fragment retains the ability to render E2F a substrate for ubiquitination. The fragment may be a C-terminal fragment of the 63 amino acid region or an internal fragment. The ability of such fragments to function as a substrate for ubiquitination may be tested by routine methods based on the accompanying examples or by attaching the fragment to an indicator protein as described below.

Similarly, we have found that the 138 C-terminal region of E2F-4 may be used, and fragments of this, also of for example 10, 20, 30, 40, 50, 100, 112 or 120 amino acids may be used as the ubiquitination domain. Again, such fragments may be internal or C-terminal.

The polypeptides used in the assay methods of the invention may contain more than one ubiquitination domain, for example from 1 to 10 such as 2, 3, 4, or 5 domains. These domains may be present in tandem repeats or in both the N- and C-terminal regions of the polypeptide.

Alternatively, the ubiquitination domain may be attached to an indicator protein such as protein which can provide a colour change when the necessary substrates are added to the cell. Usually such attachment is by preparing a fusion protein encoded by nucleic acid which links sequence encoding the domain to sequence encoding the indicator protein, the linkage being in-frame. This may be accomplished by routine cloning techniques. The domain may be N- or C-terminal to the indicator protein. Such indicator proteins include lacZ or horseradish peroxidase. In this embodiment of the assay the effect of the candidate inhibitor may be measured by adding the necessary colour change substrates in the presence and absence of the candidate and measuring the amount of colour change produced.

Alternatively, the indicator polypeptide can be a sequence specific transcription activator and the assay can include a reporter construct which is expressed in the presence of the sequence specific transcription activator. Such activators include, for example, VP16 activator of herpes virus or the GAL4 activator of yeast.

Where the assay of the invention is conducted in a host cell and the various components of the assay are provided on expression vectors the expression vectors may use any suitable promoter capable of functioning in the host cell. We have used promoters from CMV although other viral or cellular promoters may be used. It is however desirable that the promoter is not regulated by E2F and is expressed independently of the cell cycle.

Where the polypeptide used in the assay of the invention is an E2F protein capable of binding to a pocket protein the pocket protein is desirably pRb, p107 or p130.

The assay may be conducted in the presence of a proteasome inhibitor such as Cbz-LLL. Where such inhibitor is added poly-ubiquitination of the polypeptide will occur and can be detected in large quantities since polypeptide-ubiquitin conjugates will accumulate in the cell and not be subject degradation in the proteasome.

Although it is preferred that the assay of the invention is used to examine inhibitors of E2F ubiquitin-mediated degradation the assay is also suitable for examining promoters of such degradation. The various preferred embodiments of the assay described above may also be used in the assay for candidate promoter substances.

The nature and amount of candidate inhibitor or promoter substances which will be used in the assay will depend on the assay format being used and the nature of the substance. These can be determined by routine trial and error by those of ordinary skill in the art. Candidate substances include peptides based on the C-terminal region of E2F which may compete with native E2F for ubiquitin in a cell. Where the assay of the invention is conducted in a host cell the amount of candidate substance used may depend on its ability to enter the cell. Methods and adjuvants for enhancing the permeability of cells are known in the art and may be used in assays of the present invention. Anywhere between sub-nanomolar to micromolar concentrations of candidate substances may be used, for example from 1 nM to 100 $\mu$M.

Thus assays of the invention may be used as the basis for rational drug design based on peptides or mimics thereof designed around the sequence of the ubiquitination domain or fragments thereof such as those described above.

Antibodies directed against the ubiquitination domain, or fragments of such antibodies which retain the ability to bind this domain (including humanized antibodies) may be used in the diagnosis, prognosis or treatment of conditions in which aberrant mutations or other loss of function in the ubiquitination domain of E2F. Such conditions will generally be those involving uncontrolled cell proliferation such as cancer.

Antibodies or fragments thereof directed against this domain, antibodies or fragments thereof against ubiquitin, and compounds which bind an E2F/DP protein heterodimer may be used singly or in combination in assays for or methods of treating uncontrolled cell proliferation.

In a separate aspect, the present invention provides vectors which encode a truncated E2F (such as E2F-1, E2F-2, E2F-3, E2F-4 or E2F-5) which do not contain a C-terminal domain capable of ubiquitination. Such polypeptides include truncated E2F-1 or E2F-4 comprising residues 1 to about 400, for example about 300, 320, 350, 375, 390, 410 or 420. The N-terminal may also be truncated by a few amino acids, for example about 5, 10, 15 or amino acids. One such polypeptide is E2F-1 1–374. Another is E2F-4 1–301. Other truncated E2F polypeptides such as those mentioned above may be made and tested in accordance with the methods described in the accompanying Examples. Alternatively, the E2F may contain a C-terminal region but that region may be modified to prevent ubiquitination of the polypeptide in a host cell, for example by internal deletion of the ubiquitination fi domain. The invention also provides vectors which encode a fusion protein of an indicator polypeptide and one or more ubiquitination domains of E2F, such polypeptides being as described above.

These truncated and modified polypeptides will be useful in delivering transcription factor E2F to a cell which is resistant to ubiquitination. Such polypeptides may thus reduce cellular proliferation since they will accumulate in a cell and mediate transcriptional repression via their interaction with pocket proteins.

Vectors encoding the various truncated and modified E2F polypeptides as well as other polypeptides described above may in the art. The accompanying Examples describe a number of suitable vectors and further vectors can be made from these by routine methods. For example, truncated or modified polypeptides may be made by site-directed mutagenesis of nucleic acid encoding the unmodified proteins. PCR cloning techniques may be used to obtain nucleic acid encoding other transcription factors not specifically cited in the Examples and these techniques can also be used to introduce changes to the naturally occurring DNA sequence in order to produce truncated or modified polypeptides.

Generally vectors for use in the invention will be DNA vectors although RNA vectors may also be used.

The invention is illustrated by the accompanying examples.

EXAMPLES p107 and adenovirus E1 increase E2F-4 and DP-1 protein levels

To investigate the effect of p107 expression on E2F-4 and DP-1 protein stability, we transiently transfected C33A cervical carcinoma cells with HA-epitope tagged E2F-4 and DP-1 expression vectors, both in the presence and absence of p107. C33A cells were transfected with 0.5 $\mu$g of pRc-HA-E2F-4, 0.5 $\mu$g of pCMV-HA-DP-1 and 0.5 $\mu$g pRc-HA-cat in combination with 5 $\mu$g pCMV-HA-p107 or 5 $\mu$g p5Xhocc4 as indicated. 36 hours after transfection, the cells were lysed and cell extracts were subjected to 7.5 w SDS-PAGE. The separated proteins were transferred to nitrocellulose and HA-tagged proteins were detected by Western analysis with mAb 12 CA5. It was found that transfection of E2F-4 and DP-1 expression vectors under the control of the CMV promoter yields only low steady state protein levels. However, co-expression of p107 caused a dramatic increase in both E2F-4 and DP-1 protein abundance. Similarly, expression of adenovirus 5 early region 1 (Ad5 E1, which directs expression of both E1A and E1B proteins), caused a significant increase in E2F-4 and DP-1 protein levels. As an internal control, we monitored the effect of p107 and Ad5 E1 on the abundance of co-transfected HA-tagged 36 kDa catalytic subunit of protein phosphatase 2A (PP2A) whose expression is under the control of the same CMV promoter as E2F-4 and DP-1. This protein was only marginally affected by expression of p107 and Ad5 E1. The same effects on E2F abundance were seen when the PP2A internal control was omitted from the transfection. Importantly, E2F-4 mRNA levels measured 36-hours post transfection by Northern analysis were not significantly affected by p107 or Ad5 E1 cotransfection. Taken together, this suggests that p107 and Ad5 E1 influence either E2F-4 and DP-1 mRNA translation or protein stability.

p107 and adenovirus E1 stabilize E2F-4 and DP-1 proteins

To investigate the effect of p107 on E2F-4 and DP-1 protein stability, we performed a pulse chase experiment. C33A cells were transiently transfected with HA-tagged E2F-4 and DP-1 expression vectors in the presence or absence of HA-tagged p107. C33A cells were transfected with 3.0 $\mu$g of pRc-HA-E2F-4 and 1.0 $\mu$g of pCMV-HA-DP-1 in combination with 10 $\mu$g pCMV-HA-p107 or with 10 $\mu$g p5Xhocc4. Thirty six hours after transfection, cells were pulse labeled for 2 hours with [$^{35}$S]-methionine-cysteine mix and chased with 10 fold excess non-radioactive methionine and cysteine for 0, 2, 4, 8 and 18 hours. Cells were lysed and immunoprecipitations were performed with mAb 12 CA5. Immunoprecipitated proteins were separated by 10% SDS-PAGE. It was found that E2F-4 protein has a short half life in the absence of cotransfected p107, whereas expression of p107 significantly increased both E2F-4 and DP-1 half life. Expression of Ad5 E1 also caused an increase in E2F-4 and DP-1 half life. We quantitated the intensities of the bands on the gel using a phosphorimager. The intensities of the [$^{35}$S] labeled proteins were measured after exposure to phosphor imager plates and calculated in comparison to proteins present at time point zero. The results of this analysis indicate that free E2F-4 has a half life of approximately 2–3 hours, whereas p107 and Ad5 E1 increase the half life to approximately 8 and 10–12 hours, respectively. These data indicate that p107 and Ad5 E1-encoded proteins interfere with proteolysis of E2F-4 and DP-1 proteins.

Next we asked whether E2F-1 was similarly affected by expression of its pocket protein partner, pRb and by Ad5 E1. We the presence of pRb and Ad5 E1 expression vectors. C33A cells were transfected with 0.5 $\mu$g of pCMV-HA-E2F-1, 0.5 $\mu$g of pCMV-HA-DP-1 and 0.5 $\mu$g pRc-HA-cat in combination with 5 $\mu$g pCMV-pRb or 5 $\mu$g p5Xhocc4. 36 hours after transfection, the cells lysed and cell extracts were subjected to 7.5% SDS-PAGE. The separated proteins were transferred to nitrocellulose and HA-tagged proteins were detected by Western analysis with mAb 12CA5. Again, expression of pRb and Ad5 E1 greatly increased E2F-1 and to a lesser extent DP-1 protein levels, although with E2F-1 an effect of both pRb and Ad5 E1 was also seen on the control PP2A catalytic subunit. This is most likely due to the fact that expression of E2F-1, but not of E2F-4, causes apoptosis, which is inhibited by pRb and the adenovirus 19 kDa E1B protein (White et al., 1992). Nevertheless, it appears that E2F-4 and E2F-1 are similarly affected by pocket protein expression and by Ad5 E1.

E2F is degraded by the ubiquitin-proteasome pathway

Many short-lived cellular proteins are targeted for degradation by the ubiquitin-proteasome pathway. A key step in this process involves the covalent attachment of multiple ubiquitin polypeptide chains to the substrate, which targets the substrate for rapid degradation by the proteasome. These ubiquitin-substrate conjugates are highly unstable and can often only be visualized by treatment of cells with proteasome inhibitors.

To ask whether the proteasome is involved in the degradation of E2F in vivo, we transfected cells with E2F-1 and DP-1 expression vectors. U2-OS cells were transfected with 5.0 $\mu$g of pMT123 (expressing HA-tagged ubiquitin protein), 5.0 $\mu$g pRc-E2F-1 and 3.0 $\mu$g pRc-DP-1 in different combinations. After twenty four hours, transfected cells were incubated overnight with 10 $\mu$M carboxybenzyl-leucyl-leucyl-leucinal (Cbz-LLL), a potent and specific inhibitor of proteasomes (Rock et al., 1994; Wiertz et al., 1996). E2F protein levels were measured by Western blotting with mAb KH95 to detect E2F-1 protein. Incubation of E2F-1 transfected cells with Cbz-LLL caused a dramatic increase in E2F-1 protein levels compared to untreated controls. In addition, treated with inhibitor, which most likely represent ubiquitin-conjugated forms of E2F-1. To verify this, we transfected cells as above with E2F-1 expression vector (non tagged) and an HA-tagged ubiquitin expression vector. After two days, cell lysates were immunoprecipitated with the anti E2F-1 monoclonal antibody KH9 S and Western blotted with 12CA5 antibody to detect ubiquitin conjugates. A smear of E2F-ubiquitin conjugates ranging from 70 kDa to several hundred kDa was observed when E2F-1 and HA-tagged ubiquitin were cotransfected and transfected cells were treated with proteasome inhibitor. No E2F-ubiquitin conjugates were seen when proteasome inhibitor was omitted or when E2F-1 and HA-tagged ubiquitin vectors were transfected separately. Together, these data suggest strongly that free E2F can be poly-ubiquitinated in vivo and that E2F-1 is degraded by the proteasome.

Further experiments were conducted in which the plasmid pRc-E2F-1 was replaced by the same amount of pRc-E2F-4. These also showed that transfected cells treated with Cbz-LLL caused an increase in E2F-4 protein levels.

A carboxyl-terminal epitope renders E2F unstable

To ask whether specific sequences in E2F-1 are responsible for its instability, we used two carboxyl-terminal deletion mutants of E2F-1. These mutants were tested for protein expression levels in transient transfection assays. C33A cells were transfected with 0.5 μg pRc-E2F-1, 0.5 μg pCMV-E2F-1 (aa. 1–284) or 0.5 μg pCMV-E2F-1 (aa. 1–374) in combination with 0.5 μg pRc-HA-cat. 36 hours after transfection, cell extracts were prepared and separated by 7.5i SDS-PAGE. Proteins were transferred to nitrocellulose and subjected to Western blot analysis either by using mAb KH20, directed against the amino terminus of E2F-1, or by using 12CA5 recognizing the HA-tagged PP2A catalytic subunit. Both E2F-1 (1-284) and E2F-1 (1-374) were expressed at significantly increased levels as compared to wild type E2F-1 (1-437) expressed in the same vector, whereas the expression of co-transfected HA-tagged PP2A catalytic subunit was not affected by either of the E2F constructs. In this experiment, the mRNA levels of wild type and mutant E2Fs were also carboxyl-terminal 63 amino acids of E2F-1 renders the protein susceptible to rapid degradation.

Since the pRb binding site on E2F-1 overlaps with the degradation signal in the carboxyl terminus of E2F-1, we tested whether the carboxyl-terminal deletion mutants of E2F-1 could still be stabilized by pRb. C33A cells were transfected with 2.0 μg pRc-E2F-1 (aa. 1–284), 2.0 μg pCMV-E2F-1 (aa. 1–374) and 2.0 μg pRc-DP-1 in combination with 10 μg pCMV-pRb. 36 hours post transfection, cell extracts were prepared and proteins were separated by 10% SDS-PAGE, transferred to nitrocellulose and subjected to Western blot analysis using mAb KH20 directed against an epitope in the amino terminus of E2F-1. We found that E2F-1 (1-284) and E2F-1 (1-374) protein abundance was not affected by co-expression of pRb.

Identically transfected cells were scraped in PBS 36 hours after transfection and total RNA was isolated, separated on an agarose gel and transferred to nitrocellulose. Northern blot analysis was performed using a full length E2F-1 cDNA probe. This showed that the mRNAs for these mutant E2Fs was also not affected by pRb expression (FIG. 6B). Together, these data suggest that pRb stabilizes E2F by shielding the epitope on E2F that is recognized by the proteolytic machinery.

Stabilization of E2F-4' correlates with pocket Protein binding

To ask whether stabilization of E2F-4 was correlated with pocket protein binding, we transfected E2F-4 with either wild-type or mutant p107 expression vectors. E2F-4 protein levels were monitored by Western blot analysis. C33A cells were transfected with E2F-4 and DP-1 expression vectors in the presence or absence of wild-type or mutant HA-tagged p107 expression vectors. Protein extracts from transfected cells, normalized for mRNA levels, were separated on a 7.5% polyacrylamide gel and E2F-4 protein and the expression level of wild-type and mutant p107 proteins were detected with 12CA5 antibody. Cotransfection of E2F-4 with wild-type p107, p107-N385, or p107-Δ27, all of which can bind E2F-4 (Zhu et al. 1995a), was found to cause E2F-4 to accumulate at higher levels. In contrast, p107-Δ28, which does not bind E2F-4 (Zhu et al. 1995a), failed to increase E2F-4 protein abundance even though this mutant was expressed at the same level as the other p107 mutants.

The complex between E2F-4 and p107 is disrupted by phosphorylation of p107 by cyclin D1/cdk4, but not by cyclin A/cdk2 or cyclin E/cdk2 (Beijersbergen et al. 1995). We therefore asked whether expression of these cyclin/cdks would affect the ability of p107 to stabilize E2F-4. C33A cells were transfected with HA-E2F-4/HA-DP-1 in the presence of HA-p107, together with various cyclin/cdk combinations. Transfected E2F-4, DP-1, and p107 proteins were detected in a Western blot with 12CA5 anti-body. It was found that expression of cyclin D1/cdk4 prevents the p107-mediated increase in E2F-4 abundance. In contrast, both cyclin E/cdk2 and cyclin A/cdk2 expression failed to interfere with p107 stabilization of E2F-4.

In quiescent cells the major E2F-4 pocket protein complex is E2F-4-p130 (Cobrinik et al. 1993; Vairo et al. 1995). We therefore asked whether p130 shared with p107 the ability to stabilize E2F-4 protein. C33A cells were transfected with HA-E2F-4/DP-1 in the presence of p107 or p130 together with cyclin D1/cdk4 or cdk4-dominant negative. E2F-4 was detected in a Western blot with 12CA5 antibody.

Expression of p130 caused a similiar increase in E2F-4 protein levels as p107. Furthermore, phosphorylation of both pocket proteins by cyclin D1/cdk4 abolished pocket protein-mediated stabilization of E2F-4, whereas expression of cdk4 dominate-negative was without effect. Taken together, these data strongly support the notion that E2F-4 is stabilized as a result of direct binding to a pocket protein partner.

A carboxy-terminal epitope renders E2F-4 unstable

The data shown above indicate that E2F-4 is unstable and that binding of pocket proteins to the carboxyl terminus of E2F-4 causes an increase in E2F-4 half-life. We therefore asked whether a carboxy-terminal deletion mutant of E2F-4, ΔE2F-4 encoding amino acids 1–301 of E2F-4 and lacking the p107 interaction surface, differed from wild-type E2-4 in stability. C33A cells were transfected with E2F-4/DP-1 or ΔE2F-4/DP-1 (expressing amino acids 1–301 of E2F-4) expression vectors in the presence or absence of p107. Protein extracts of transfected cells were normalized for mRNA content. E2F-4 protein was detected in a Western blot with C-108 antibody. Northern blot of RNA from transiently transfected cells probed with E2F-4 CDNA after normalization for equal amounts of E2F-4 and ΔE2F-4 mRNA (see Materials and Methods). E2F-4 and ΔE2F-4 were immuno-precipitated with 12CA5 antibody. After normalization for mRNA levels in transfected cells, ΔE2F-4 was expressed at a substantially higher level as compared with wild-type E2F-4. Pulse-chase experiments using both wild-type E2F-4 and ΔE2F-4 were also conducted. Cells were pulse-labeled with [$^{35}$S] methionine-cysteine mix and chased with excess cold amino acids. The experiments revealed that the difference in protein accumulation was caused by a significantly prolonged half-life of the ΔE2F-4 protein as compared with the wild-type E2F-4 protein (2 hr vs. 18 hr). Thus, the carboxy-terminal 112 amino acids of E2F-4 harbors an epitope that renders the protein unstable. Significantly, expression of p107 caused an increase in wild-type E2F-4 abundance, but did not affect protein levels of ΔE2F-4. As an additional control for specificity, we showed that the abundance of p27, a labile nuclear protein that does not interact with p107 (Polyak et al. 1994; Toyoshima and Hunter 1994), was also affected by p107. Taken together, these data support the notion that binding of E2F-4 to p107 causes the protein to be stable and that p107 does not influence protein stability non-specifically.

The carboxyl terminus of E2F-4 renders a yeast transcription factor unstable

Human U2-OS osteosarcoma cells were transfected with expression vectors that direct the synthesis of the DNA binding domain of yeast GAL4 (amino acids 1–147) fused to the carboxyl terminus of human E2F-4 (amino acids 276–413) or yeast GAL4 (1–147) or were co-transfected with GAL4-E2F-4 chimeric vector and p107 expression vector. Two days after transfection, lysates were prepared from transfected cells and the abundance of the GAL4 proteins was detected in a western blot using a monoclonal antibody to the DNA binding domain of GAL4. In the absence of p107, the amount of GAL4-E2F-4 (276–413) fusion protein observed was less than GAL4 alone. Co-transfection of the GAL4-E2F-4 vector and p107 restored levels of the GAL4-E2F fusion to those of GAL4 alone. Since in all three transfections equal amounts of GAL4 mRNA were detected, we conclude that the reduced abundance of the GAL4-E2F-4 fusion protein as compared to the parental GAL4 (1–147) protein is the result of reduced protein stability of the GAL4-E2F-4 protein.

E2F-4 is unstable in yeast

We have found that yeast (S.cerevisiae) has the ability to degrade E2F through ubiquitination. Our recent data indicate that wild type E2F is unstable in yeast whereas a C-terminally truncated E2F-4 is more stable. Yeast strain Y190 was transformed with yeast expression vectors (pPC97) that direct the synthesis of either wild type E2F-4 or the C-terminally truncated E2F-4 encoding amino acids 1–301 of E2F-4. Protein lysates were made from two duplicate exponentially growing yeast cultures and analyzed for E2F protein levels by Western blot analysis using anti E2F-4 monoclonal antibody. Equal amounts of wild type or mutant E2F-4 mRNA were expressed by the yeast cultures, but at the protein level amounts of the ΔE2F-4 were several-fold higher, indicating that the truncation renders the protein more stable.

Discussion

We show here that both the E2F and DP components of E2F transcription factors are unstable. Two lines of evidence indicate that E2F is a substrate of the ubiquitin-proteasome system of targeted proteolysis. First, incubation of cells with a specific inhibitor of the proteasome leads to a significant accumulation of E2F protein. Furthermore we show that in cells treated with proteasome inhibitor, significant amounts of E2F-poly-ubiquitin conjugates accumulate. Poly-ubiquitination is known to act as a sorting signal which targets proteins for rapid degradation by the proteasome (Chau et al., 1989). We have mapped the domain that renders E2F-1 unstable to the carboxyl terminal 63 residues, which is in close proximity to the pRb binding site of E2F-1 (Helin et al., 1992; Kaelin et al., 1992). Our data indicate that binding of pRb or p107 to E2F/DP heterodimers protects both polypeptides from degradation. Our data suggest a model in which pocket proteins inhibit E2F degradation by shielding the carboxyl-terminal epitope on E2F that is recognized by the ubiquitination machinery. Consistent with this, we found that carboxyl-terminal deletion mutants of E2F could not be stabilized further by pocket protein expression. Surprisingly, we found that adenovirus E1 proteins also cause a stabilization of E2F and DP proteins. This was unexpected because E1A is known to disrupt E2F-pocket protein complexes, and should therefore generate free, but unstable, E2F. We propose that the stabilization of E2Fs by Ad5 E1 serves to enhance S phase entry of adenovirus infected cells: By preventing the degradation of E2F released from pocket protein complexes, E1A causes a further increase in free E2F transcription factors, which in turn facilitate S phase entry of adenovirus-infected cells.

How E1A mediates stabilization of free E2F is at present not clear. We have recently shown that E1A can interact with a member of the family of ubiquitin conjugating enzymes, named mUBC9, thus providing a possible link between adenovirus transforming proteins and the ubiquitin-proteasome pathway (Hateboer et al., 1996). This protein is highly related to a S. cerevisiae protein UBC9, whose inactivation causes an arrest in the S and G2 phases of the cell cycle (Seufert et al., 1995). Importantly, the E1A-interacting mUBC9 complements the yeast cell cycle defect, indicating that mUBC9 can contribute to yeast cell cycle regulation (Hateboer et al., 1996). Whether UBC9 plays a role in targeted proteolysis of E2Fs remains to be investigated.

E2F-pocket protein complexes are thought to play an active role in maintaining quiescence by acting as dominant repressors of transcription (Weintraub et al., 1995; Weintraub et al., 1992). As such, E2F-pocket protein complexes may prevent expression of genes that are activated by mitogenic signals. In most types of resting cells, the main E2F that is expressed is E2F-4 which is bound to p130 during quiescence (Cobrinik et al., 1993; Sardet et al., 1995; Vairo et al., 1995) The observed stability to P2F-4-pocket protein complexes may be required to maintain active transcriptional repression in quiescent cells that have low de novo synthesis of E2F polypeptides. Cell cycle entry is accompanied by an increase in E2F transcription and an increase in free E2F transcription factor (Sardet et al., 1995). The rapid turn over of free E2F may prevent accumulation of excess free E2F, which is known to induce apoptosis (Qin et al., 1994; Wu and Levine, 1994). That the cell has devised other mechanisms to limit the activity of E2F was recently shown by Krek et al. Cyclin A can directly interact with E2F-1, which mediates down-regulation of E2F DNA binding activity during S phase (Krek, 1994). Mutants of E2F-1 that are resistant to down-regulation by cyclin A induce apoptosis, probably by hyper-stimulation of E2F-1 responsive genes (Krek et al., 1995). Our present data uncover another level of regulation of E2F transcription factors. By active degradation of free E2F, but not pocket protein bound E2F, the cell inhibits degradation of E2F pocket protein complexes in quiescent cells and prevents accumulation of high levels of free E2F in proliferating cells.

Experimental Procedures

Plasmids pCMV-HA-E2F-1, pRc-E2F-1, pCMV-HA-DP-1, pCMV-E2F-1 (1–284) and pCMV-E2F-1 (1–374) were generous gifts of K. Helin. Mutant p107 expression vectors were provided by L. Zhu (Massachusetts General Hospital Cancer Center, Charlestown). pRc-HA-E2F-4 and p5Xhocc4, expressing the entire early region 1 (E1) of adenovirus type 5 have both been described previously (Beijersbergen et al., 1995) (Bernards et al., 1982). PΔE2F-4, expressing amino acids 1–310 of E2F-4, was made by PCR and cloned in pRc-CMv, downstream of an HA epitope. pMT123, expressing an HA-tagged ubiquitin protein was kindly provided by D. Bohmann (Treier et al., 1994). pRc-DP-1 and pRc-HA-cat were gifts from M. Voorhoeve. pCMV-HA-p107 and pCMV-pRb have been described previously (Beijersbergen et al., 1995; Beijersbergen et al., 1994).

Cell culture, transfections, labeling and pulse-chase experiments

Human osteosarcoma U2-OS cells and human cervical carcinoma (DMEM) supplemented with 10% fetal calf serum (FCS). Transfections were performed overnight using the calcium phosphate method. After this, cells were re-fed with normal medium and 36 hours post-transfection, cells were either lysed directly in SDS-containing sample buffer to obtain whole cell lysates, or lysed in RIPA$^+$ (RIPA buffer supplemented with a cocktail of protease inhibitors, Complete, Boehringer Mannheim) and subjected to immunoprecipitations. For pulse labeling and chase experiments in the presence or absence of pocket proteins or adenovirus E1, cells were starved for 1 hour in methionine/cysteine free medium and subsequently incubated with 100 µCi of [$^{35}$S] methionine/cysteine per 100 mm dish for 2 hours. Then, cells were lysed in RIPA$^+$ on ice for 30 minutes or incubated with normal medium supplemented with a 10-fold excess of non-radioactive methionine and cysteine for the indicated periods of time and lysed in RIPA$^+$ thereafter. Equal amounts of radioactive lysates were incubated at 4° C. for 30 minutes with 5 µl non-immune serum for preclearing. Subsequently, lysates were incubated for 2 hours at room temperature with specific antibodies, pre-complexed on protein A-sepharose beads. Immunoprecipitates were washed four times in RIPA, heated in SDS containing sample buffer and loaded on a SDS-7.5% polyacrylamide gel.

Northern blotting

Total RNA was isolated from transiently transfected cells 36 hours post-transfection using the NP-40 lysis method. Equal amounts of RNA were separated on a 1% formaldehyde-agarose gel. After electrophoresis, RNA was transferred to a nitrocellulose filter and hybridized with a full length E2F-1 and E2F-4 cDNA probes. Equal loading of the gel was checked by ethidium bromide staining.

Immunoblotting

For the abundance of E2F wild type and E2F mutant proteins in the presence or absence of pocket proteins and adenovirus E1, whole cell lysates (10% of a transiently transfected 100 mm dish) were separated on SDS-10% or SDS-7.5% polyacrylamide gels, as indicated. Non-radioactive E2F immunoprecipitates, collected by protein A-sepharose beads, were separated on a SDS-10% polyacrylamide gel. Proteins were transferred from gels to nitrocellulose filters by electrophoresis. Filters were blocked in PBS supplemented with 0.1% Tween-20 and 5% non-fat milk (Protifar, Nutricia) (TPBS, 5%) for 2 hours at room temperature. Subsequently, filters were either incubated with 12CA5 hybridoma supernatant (directed against the HA-tag) in a dilution of 1:20, or with KH95 hybridoma supernatant (directed against the carboxyl terminus of E2F-1) in a dilution of 1:10,000, or with KH20 monoclonal antibody (directed against the amino terminus of E2F1) in a dilution of 1:500 for 3 hours in TPBS, 2% at room temperature and incubated with secondary antibody for 30 minutes at room temperature in TPBS, 2%. Filters were washed three times in TPBS and visualization was performed by enhanced chemiluminescence (Amersham).

E2F-1 ubiquitination

U2-OS cells were transiently transfected with 5 µg pMT123 (HA-tagged ubiquitin), 5 µg pRc-E2F-1 and 5 µg pRc-DP-1 in different combinations. The total amount of transfected DNA per dish was adjusted up to 17 µg with empty vector (pRc/CMV). 24 hours post-transfection, cells were incubated overnight with the proteasome inhibitor Cbz-LLL in a final concentration of 10 µg in DMEM/10% FCS or re-fed with normal medium. Then, cells were lysed in RIPA$^+$ for 30 minutes on ice. Immunoprecipitations were performed with 2 µl KH95 monoclonal antibody (Santa Cruz) pre-complexed on 20 µl protein A-sepharose beads for 2 hours at 4° C. Beads were washed four times in RIPA, heated in SDS containing sample buffer and separated on a SDS-10% polyacrylamide gel. Transfer to nitrocellulose was performed overnight and the filter was incubated with 12CA5 hybridoma supernatant directed against HA-tagged ubiquitin. To detect E2F-ubiquitin conjugates, U2-OS cells were transiently transfected with 5 µg pRc-E2F-1 and 5 µg pRc-DP-1, adjusted to 17 µg with pRc/CMV or with 17 µg empty vector. 24 hours post-transfection, cells were incubated overnight with medium containing 10 µM Cbz-LLL or re-fed with normal medium. Subsequently, cells were lysed directly in SDS containing sample buffer, and the lysates were separated over a SDS-10% polyacrylamide gel and immunoblotted with KH95 against E2F-1 protein.

References

Beijersbergen, R. L., and Bernards, R. (1996). Cell cycle regulation by the retinoblastoma family of growth inhibitory proteins. Biochem. Biophys. Acta, Reviews on Cancer. 1287, 103–120.

Beijersbergen, R. L., Carlée, L., Kerkhoven, R. M., and Bernards, R. (1995) Regulation of the retinoblastoma-related p107 by G1 cyclin complexes. Genes & Dev. 9, 1340–1353.

Beijersbergen, R. L., Kerkhoven, R., Zhu, L., Carlée, L., Voorhoeve, P. M., and Bernards, R. (1994). E2F-4, a new member of the E2F gene family, has oncogenic activity and associates with p107 in vivo. Genes & Dev. 8, 2680–2690.

Bernards, R., Houweling, A., Schrier, P. I., Bos, J. L., and Van der Eb, A. J. (1982). characterization of cells transformed by Ad5/Ad12 hybrid early region 1 plasmids. Virology 120, 422–432.

Chau, V., Tobias, J. W., Bachmair, A., Marriott, D., Ecker, D. J., Gonda, D. K., and Varshavsky, A. (1989). A multiubiquitin chain is confined to specific lysine in a targeted short-lived protein. Science 243, 1576–1583.

Chittenden, T., Livingston, D. M., and DeCaprio, J. A. (1993). Cell cycle analysis of E2F in primary human T cells reveals novel E2F complexes and biochemically distinct forms of free E2F. Mol Cell Biol 13, 3975–3983.

Cobrinik, D., Whyte, P., Peeper, D. S., Jacks, T., and Weinberg, R. A. (1993). Cell cycle-specific association of E2F with the p130 E1A-binding protein. Genes Dev 7, 2392–2404.

Degregori, J., Kowalik, T., and Nevins, J. R. (1995). Cellular targets for activation by the E2F1 transcription factor include DNA synthesis- and G1/S-regulatory genes. Mol. Cell. Biol. 15, 4215–4224.

Deshaies, R. J., Chau, V., and Kirschner, M. W. (1995). Ubiquitination of the G1 cyclin Cln2p by a Cdc34p-dependent pathway. EMBO J. 14, 303–312.

Dowdy, F. D., Hinds, P. W., Louie, K., Reed, S. I., and Weinberg, R. A. (1993). Physical interaction of the retinoblastoma protein with Human D cyclins. Cell 73, 499–511.

Ewen, M. E., Sluss, H. K., Sherr, C. J., Matsushime, H., Kato, J., and Livingston, D. M. (1993). Functional interactions of the retinoblastoma protein with mammalian D-type cyclins. Cell 73, 487–497.

Farnham, P. J., Slansky, J. E., and Kollmar, R. (1993). The role of E2F in the mammalian cell cycle. [Review]. Biochim Biophys Acta 1155, 125–131.

Ginsberg, D., Vairo, G., Chittenden, T., Xiao, Z.-X., Xu, G., Wydner, K. L., DeCaprio, J. A., Lawrence, J. B., and Livingston, D. M. (1994). E2F-4, a new E2F transcription factor family member, interacts with p107 and has transforming potential. Genes & Dev. 8, 2665–2679.

Glotzer, M., Murray, A. W., and Kirschner, M. W. (1991). Cyclin is degraded by the ubiquitin pathway. Nature 349, 132–138.

Goebl, M. G., Goetsch, L., and Byers, B. (1994). The Ubc3 (Cdc34) ubiquitin-conjugating enzyme is ubiquitinated and phosphorylated in vivo. Mol Cell Biol 14, 3022–3029.

Haas, A. L., and Rose, I. A. (1982). The mechanism of ubiquitin activating enzyme. A kinetic and equilibrium analysis. J. Biol. Chem. 257, 10329–10337.

Hateboer, G., Hijmans, E. M., Nooij, J. B. D., Schlenker, S., Jentsch, S., and Bernards, R. (1996). mUBC9, a novel adenovirus E1A-interacting protein that complements a yeast cell cycle defect. J. Biol. Chem. In press.

Helin, K., Lees, J. A., Vidal, M., Dyson, N., Harlow, E., and Fattey, A. (1992). A cDNA encoding a pRB-binding protein with properties of the transcription factor E2F. Cell 70, 337–350.

Hiebert, S. W., Lipp, M., and Nevins, J. R. (1989). E1A-dependent trans-activation of the human MYC promoter is mediated by the E2F factor. Proc Natl Acad Sci USA 86, 3594–3598.

Hijmans, E. M., Voorhoeve, P. M., Beijersbergen, R. L., van 't Veer, L. J., and Bernards, R. (1995). E2F-5, a new E2F family member that interacts with p130 in vivo. Mol. Cell. Biol. 15, 3082–3089.

Hilt, W., and Wolf, D. H. (1996). Proteasomes: destruction as a programme. Trends Biochem. Sci. 21, 96–102.

Hinds, P. W., Mittnacht, S., Dulic, V., Arnold, A., Reed, S. I., and Weinberg, R. A. (1992). Regulation of retinoblastoma protein functions by ectopic expression of human cyclins. Cell 70, 993–1006.

Hochstrasser, M. (1995). Ubiquitin, proteasomes, and the regulation of intracellular protein degradation. Curr. Opin. Cell Biol. 7, 215–223.

Jentsch, S. (1992). The ubiquitin-conjugation system. [Review]. Annu Rev Genet 26, 179–207.

Jentsch, S., and Schlenker, S. (1995). Selective protein degradation: a journey's end within the proteasome. Cell 82, 881–884.

Johnson, D. G., Cress, W. D., Jakoi, L., and Nevins, J. R. (1994). Oncogenic capacity of the E2F1 gene. Proc Natl Acad Sci USA 91, 12823–12827.

Johnson, D. G., Ohtani, K., and Nevins, J. R. (1994). Autoregulatory control of E2F1 expression in response to positive and negative regulators of cell cycle progression. Genes Dev 8, 1514–1525.

Kaelin, W. G., Krek, W., Sellers, W. R., DeCaprio, J. A., Ajchenbaum, F., Fuchs, C. S., Chittenden, T., Li, Y., Farnham, P., Blanar, M. A., Livingston, D. M., and Flemington, E. K. (1992). Expression cloning of a cDNA encoding a retinoblastoma-binding protein with E2F-like properties. Cell 70, 351–364.

Krek, W., Ewen, M. E., Shirodkar, S., Arany, Z., Kaelin, Jr., W. G. and Livingston, D. M. (1994). Negative regulation of the growth promoting transcription factor E2F-1 by a stably bound cyclin A-dependent protein kinase. Cell 78, 161–172.

Krek, W., Xu, G., and Livingston, D. M. (1995). cyclin A-kinase regulation of E2F-1 DNA binding function underlies suppression of an S phase checkpoint. Cell 83, 1149–1158.

Lam, E. W., and Watson, R. J. (1993). An E2F-binding site mediates cell-cycle regulated repression of mouse B-myb transcription. Embo J 12, 2705–2713.

Lees, E., Faha, B., Dulic, V., Reed, S. I., and Harlow, E. (1992). Cyclin E/cdk2 and cyclin A/cdk2 kinases associate with p107 and E2F in a temporally distinct manner. Genes & Dev. 6, 1874–1885.

Neuman, E., Flemington, E. K., Sellers, W. R., and Kaelin, W. J. (1994). Transcription of the E2F-1 gene is rendered cell cycle dependent by E2F DNA-binding sites within its promoter. Mol Cell Biol 14, 6607–6615.

Oswald, F., Lovec, H., Moroy, T., and Lipp, M. (1994). E2F-dependent regulation of human MYC: trans-activation by cyclins D1 and A overrides tumour suppressor protein functions. Oncogene 9, 2029–2036.

Pagano, M., Tam, S. W., Theodoras, A. M., Beer-Romero, P., Del Sal, G., Chau, V., Yew, P. R., Draetta, G. F., and Rolfe, M. (1995). Role of the ubiquitin-proteasome pathway in regulating abundance of the cyclin-dependent kinase inhibitor p27. Science 269, 682–685.

Pickart, C. M., and Rose, I. A. (1985). Functional heterogeneity of ubiquitin carrier proteins. J. Biol. Chem. 260, 1573–1581.

Polyak et al., (1994). Cloning of p27Kip1, a cyclin dependent inhibitor and potential mediator of extracellular entimitogenic signals. Cell 78, 59–66.

Qin, X. Q., Livingston, D. M., Kaelin, W. J., and Adams, P. D. (1994). Deregulated transcription factor E2F-1 expression leads to S-phase entry and p53-mediated apoptosis. Proc Natl Acad Sci USA 91, 10918–10922.

Rock, K. L., Gramm, C., Rothstein, K., Clark, K., Stein, R., Dick, L., Hwang, D., and Goldberg, A. L. (1994). Inhibitors of the proteasome block the degradation of most cell proteins and the generation of peptides presented on MHC class I molecules. Cell 78, 761–777.

Rubin, D. M., and Finley, D. (1995). Proteolysis. The proteasome: a protein-degrading organelle? Curr. Biol. 5, 854–858.

Sardet, C., Vidal, M., Cobrinik, D., Geng, Y., Onufryk, C., Chen, A., and Weinberg, R. A. (1995). E2F-4 and E2F-5, two members of the E2F family, are expressed in the early phases of the cell cycle. Proc Natl Acad Sci USA 92, 2403–2407.

Schwob, E., Bohm, T., Mendenhall, M. D., and Nasmyth, K. (1994). The B-type cyclin kinase inhibitor p40SIC1 controls the G1 to S transition in S. cerevisiae. Cell 79, 233–244.

Seufert, W., Futcher, B., and Jentsch, S. (1995). Role of a ubiquitin-conjugating enzyme in degradation of S- and M-phase cyclins. Nature 373, 78–81.

Shirodkar, S., Ewen, M., DeCaprio, J. A., Morgan, J., Livingston, D. M., and Chittenden, T. (1992). The transcription factor E2F interacts with the retinoblastoma product and a p107-cyclin A complex in a cell cycle-regulated manner. Cell 68, 157–166.

Singh, P., Wong, S. H., and Hong, W. (1994). Overexpression of E2F-1 in rat embryo fibroblasts leads to neoplastic transformation. Embo J 13, 3329–3338.

Toyoshima and Huntar (1994). P27, a novel inhibitor of G1 cyclin-Cdk protein kinase activity, is related to p21. Cell 78, 787–798.

Treier, M., Staszewski, L. M., and Bohmann, D. (1994). Ubiquitin-dependent c-Jun degradation in vivo is mediated by the delta domain. Cell 78, 787–798.

Vairo, G., Livingston, D. M., and Ginsberg, D. (1995). Functional interaction between E2F-4 and p130: evidence for distinct mechanisms underlying growth suppression by different retinoblastoma protein family members. Genes Dev 9, 869–881.

Weintraub, S. J., Chow, K. N. B., Luo, R. X., Zhang, S. H., He, S., and Dean, D. C. (1995). Mechanisms of active transcriptional repression by the retinoblastoma protein. Nature 375, 812–815.

Weintraub, S. J., Prater, C. A., and Dean, D. C. (1992). Retinoblastoma protein switches the E2F site from positive to negative element. Nature 358, 259–261.

White, E., Sabbatini, P., Debbas, M., Wold, W. S., Kusher, D. I., and Gooding, L. R. (1992). The 19-kilodalton adenovirus E1B transforming protein inhibits programmed cell death and prevents cytolysis by tumor necrosis factor alpha. Mol Cell Biol 12, 2570–2580.

Whyte, P., Buchkovich, K. J., Horowitz, J. M., Friend, S. F., Raybuck, M., Weinberg, R. A., and Harlow, E. (1988).

Association between an oncogene and an anti-oncogene: the adenovirus E1A proteins bind to the retinoblastoma gene product. Nature 334, 124–129.

Wiertz, E. J. H. J., Jones, T. R., Sun, L., Bogyo, M., Geuze, H. J., and Ploegh, H. L. (1996). The human cytomegalovirus US11 gene product dislocates MHC class I heavy chains from the endoplasmic reticulum to the cytosol. Cell 84, 769–779.

Wu, X., and Levine, A. J. (1994). p53 and E2F-1 cooperate to mediate apoptosis. Proc Natl Acad Sci USA 91, 3602–3606.

Yaglom, J., Linskens, M. H., Sadis, S., Rubin, D. M., Futcher, B., and Finley, D. (1995). p34Cdc28-mediated control of Cln3 cyclin degradation. Mol Cell Biol 15, 731–741.

Zhu, L., Zhu, L., Xie, E., and Chang, L.-S. (1995). Differential roles of two tandem E2F sites in the repression of the human p107 promotor by retinoblastoma and p107 proteins. Mol. Cell. Biol. 15, 3552–3562.

Zhu, L. et al, (1995a). The pRB-related protein p107 contains two growth suppression domains. EMBO J. 14, 1904–1913.

---

What is claimed is:

1. An assay method for an inhibitor of transcription factor E2F ubiquitin-mediated degradation which method comprises:
   a) bringing a polypeptide which contains a domain which renders a protein selected from the group consisting of E2F-1, E2F-2, E2F-3, E2F-4 and E2F-5 a substrate for ubiquitination into contact with a candidate inhibitor; and
   b) determining whether or not the candidate inhibitor is capable of reducing ubiquitination of said polypeptide.

2. An assay according to claim 1 wherein the polypeptide is a fusion protein which comprises an indicator polypeptide.

3. An assay according to claim 2 wherein the indicator polypeptide is LacZ.

4. An assay according to claim 1 wherein the domain which renders E2F a substrate for ubiquitination comprises the 63 amino acid C-terminal region of E2F-1 recited in SEQ ID NO:2.

5. An assay according to claim 1 wherein the polypeptide is expressed in a host cell from a recombinant expression vector.

6. An assay according to claim 5 wherein the expression vector comprises a CMV promoter operably linked to a sequence encoding the polypeptide.

7. An assay according to claim 5 wherein a DP-1 polypeptide is co-expressed in the host cell.

8. An assay according to claim 1 wherein the assay is conducted in the presence of a proteasome inhibitor.

9. An assay according to claim 1 wherein the determining of whether or not the candidate inhibitor is capable of reducing ubiquintination of said polypeptide is performed by providing ubiquitin and determining the amount of said ubiquitin which has been bound to said polypeptide.

10. An assay according to claim 9 wherein the assay is performed in a host cell which contains an expression vector capable of expressing ubiquitin.

11. An assay according to claim 10 wherein the ubiquitin is tagged with an HA epitope capable of binding to a monoclonal antibody.

12. An assay method for an enhancer of transcription factor E2F ubiquitin-mediated degradation which method comprises:
   a) bringing a polypeptide which contains a domain which renders a protein selected from the group consisting of E2F-1, E2F-2, E2F-3, E2F-4 and E2F-5 a substrate for ubiquitination into contact with a candidate enhancer; and
   b) determining whether or not the candidate enhancer is capable of enhancing ubiquitination of said peptide.

13. The assay method according to claim 1 wherein said protein is selected from the group consisting of E2F-1 and E2F-4.

14. The assay method according to claim 12 wherein said protein is selected from the group consisting of E2F-1, and E2F-4.

15. An assay according to claim 12, wherein the polypeptide is an E2F protein or fragment thereof which is capable of binding to a pocket protein.

* * * * *